(12) United States Patent
Smith

(10) Patent No.: US 8,747,916 B1
(45) Date of Patent: Jun. 10, 2014

(54) SELECTING, PRODUCING, AND FEEDING WHOLE ALGAE AS A FEED SUPPLEMENT FOR CATTLE AND BISON TO PRODUCE MEAT HIGH IN OMEGA 3'S FOR HUMAN HEALTH

(71) Applicant: Donald M. Smith, Oklahoma City, OK (US)

(72) Inventor: Donald M. Smith, Oklahoma City, OK (US)

( * ) Notice: Subject to any disclaimer, the term of this patent is extended or adjusted under 35 U.S.C. 154(b) by 0 days.

(21) Appl. No.: 13/663,972

(22) Filed: Oct. 30, 2012

(51) Int. Cl.
*A01N 65/00* (2009.01)

(52) U.S. Cl.
USPC .......................................... 424/725

(58) Field of Classification Search
None
See application file for complete search history.

(56) References Cited

U.S. PATENT DOCUMENTS

| | | |
|---|---|---|
| 4,911,944 A | 3/1990 | Holub |
| 5,290,753 A | 3/1994 | Newhouse et al. |
| 5,932,257 A | 8/1999 | Wright et al. |
| 7,504,121 B2 | 3/2009 | Abril et al. |
| 8,232,090 B2 | 7/2012 | Kallenmareth et al. |

*Primary Examiner* — Michael Meller
(74) *Attorney, Agent, or Firm* — Fish & Richardson P.C.

(57) ABSTRACT

The present invention is a system and method for creating and using algae as a food supplement for cattle and buffalo thereby providing a desirable food supplement for cattle and buffalo wherein the meat and fat produced has increased specific Omega-3 polyunsaturated fatty acids for a product, which imparts a healthier cardiovascular or healthier central nervous system.

4 Claims, 1 Drawing Sheet

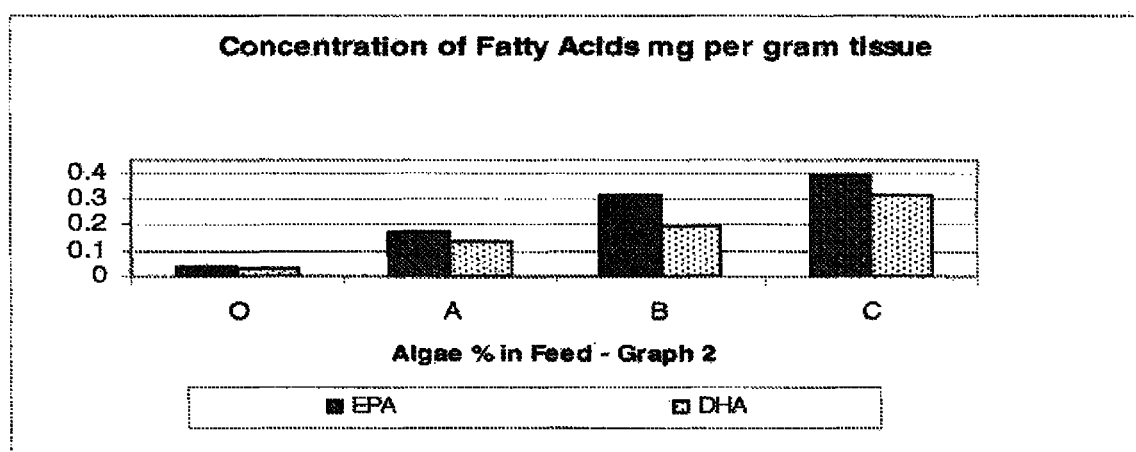

SELECTING, PRODUCING, AND FEEDING WHOLE ALGAE AS A FEED SUPPLEMENT FOR CATTLE AND BISON TO PRODUCE MEAT HIGH IN OMEGA 3'S FOR HUMAN HEALTH

BACKGROUND OF THE INVENTION

1. Field of the Invention

In general, the present invention is a composition, system and method of creating and using whole algae as a food supplement for animals. The algae are high in omega 3s DHA and or EPA (and other constituents) in relation to total fats, and are suitable for cattle and bison's digestive system. The resulting meat with high DHA and EPA provides a superior beef with heart healthy properties and other healthy properties for the consumer.

2. Description of the Prior Art

There is a current recognition of the diverse benefits of algae as a nutritional supplement, a potential biofuel, and with some technologies for growing as a means to capture excess or unwanted $CO_2$. The field of algae growth, harvesting and processing is burgeoning and hundreds of millions of dollars are being invested into this industry, mostly aimed at identifying the most promising strains of algae for biofuel and developing prototype cultivation facilities for their growth. Additionally, more recently, algae growers are focusing on growing algae high in Omega 3's and to process the algae into its constituents, with the Omega 3's being of very high value and then producing biofuel with the remaining fats, and having a residual for other constituents including a byproduct animal feed high in protein. Algae may someday achieve the game changing ability to convert renewable sunlight into transportation fuel. Sustainable transportation fuel was the hope underlying corn based ethanol but the reality is that energy yields from corn are too low, while the use of prime cropland to grow ethanol feedstock has crowded our agricultural system.

Algae is nature's most basic photosynthesis organism. Some algae consume water, sunlight and carbon dioxide ($CO_2$) to produce sugars. Those sugars and reduced high-energy compounds eventually produce the lipids, which can be readily processed into biofuel that can be used in place of diesel fuel. Corn grown on America's best farmland can yield less than 200 gallons per acre of bioethanol. Experts agree that algae can yield more than 25 times the energy density of corn-derived biofuel; algae grown on an acre of wasteland (requiring only decent sunlight) can yield anywhere between 2,000 and 7,000 gallons of biofuel per year. Algae may be a biofuel competitive with diesel oil priced at $2.00 to $3.00 per gallon if algae can be found or made to grow faster, or the algae can be modified genetically to refine fuel such as gasoline, which is then excreted through the cell wall of the algae so it does not have to be processed. However, algae, which is heterotrophic, can use organic carbon sources in the water, such as sugar under fermentation, or glucose, as a substitute for sunlight, or in addition to sunlight. This patent focusses on the growth of such heterotrophic algae for use as an animal feed supplement, because there are now available techniques for growing such algae that are much less expensive than former methods. While this growing technique does not directly use CO2 from power plant and ethanol plant emissions, there is CO2 removed from the atmosphere by the plant, sugar cane, which uses the CO2 (from power plant or ethanol plant emissions) in the photosynthetic process. The heterothophic algae also commonly have silica cell walls making less likely to break in the rumen, and leave the omega 3's intact when released in the small intestine.

There are two groups of essential fatty acids, Omega-3 fatty acids and Omega-6 fatty acids. Omega-3 fatty acids are found naturally in the oil of cold-water fish, such as mackerel, salmon, sardines, anchovies and tuna, or as extracted oil from plants, such as flaxseed, canola (rapeseed), or soybean. Examples of Omega-3 fatty acids include docosahexaenoic acid (DHA), eicosapentenoic acid (EPA) and alpha linolenic acid (ALA). Of key importance, the Omega 3's EPA and DHA are found in large amounts only in cold-water fish, and not in land animals or seeds. Hence, to obtain large amounts of EPA and DHA, humans need eat oily fish or take oil supplements, which are made from fish or from the algae that form the base of the food chain for fish. ALA, in contrast, is found abundantly in seeds such as flax. Omega-3 fatty acids are linked to a wide variety of beneficial health effects in documented intervention studies as essential constituents of cells, especially brain cells, nerve cells, retina, adrenal glands, and reproductive cells. Long chain Omega-3 polyunsaturates (PUFA's) such as DHA&EPA are thought to have health benefits for the heart, skin, and immune system and help regulate inflammatory diseases, attention deficit disorders and infant development. There are also a number of new studies underway that suggest benefits in preventing Alzheimer's, dementia, colorectal cancers, and reducing deaths due to heart disease.

There have been a number of patents granted outlining the benefits from specific Omega fatty acids present in food and/or supplements. Several patents have also been granted for the enrichment of foods that are normally low or deficient in Omega-3/6 and PUFA's. For example, U.S. Pat. No. 5,932,257 (Wright et al.) relates to DHA being produced in cow's milk through the feeding of cold-water fishmeal to cows, using a feather meal based feed supplement. The feather meal used according to this prior art reference is used as an inhibitor of microbial degradation of DHA in the rumen of the dairy cattle. U.S. Pat. Nos. 4,911,944 and 5,290,573 also disclose the use of feed supplements containing fishmeal combined with animal by-products e.g. feather meal, bone meal and the like. A number of patents have also been granted for the elevation of Omega-3 in eggs using flax meal or algae/DHA feed supplements in chickens.

In terms of algae, (DHA fermented concentrates), these feed and food mixes are produced via genetic recombination technology, which has limited consumer favor in most markets. Prior art feed formulas have a number of deficiencies on a practical basis. For example, fish meal/feather meal feed supplements are very unpalatable and can be a feeding deterrent to livestock such as cows, and only limited amounts of DHA can be achieved in the milk. Also, the use of animal by-products, i.e., blood meal/feather meal, have been banned in most countries to prevent the spread of infectious diseases.

There is a need in the art for feed supplements capable of elevating the amount of Omega-3 fatty acids in beef The above discussed limitations in the prior art is not intended to be exhaustive. The current invention provides a solution not currently found in the known art.

SUMMARY OF THE INVENTION

In view of the foregoing disadvantages inherent in the known types of algae food supplements the present invention provides a new and improved effective algae based food supplement for beef cattle and or buffalo where the prior art fails. As such, the general purpose of the present invention, which will be described subsequently in greater detail, is to provide a new and improved method of creating an algae based food supplement and means to reduce $CO_2$ which has all the advantages of the prior art and none of the disadvantages.

To attain this, the present invention essentially comprises a system and method for taking commonly available carbohydrates such as sugar, which consume CO2 in the atmosphere, and feeding it to algae. The invention also cultivates algae for a specific use, and feeds it to cattle improving the cardiovascular health of the beef consumer by increasing specific Omega-3 polyunsaturated fatty acids (PUFAs) in the muscle tissue of beef.

It is further contemplated the invention may be utilized for the general feeding of other animals, such as but not limited to buffalo. It is contemplated that buffalo may be used a livestock for meat.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction, arrangement of the components, and amounts thereof set forth in the following description. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other compositions, methods, and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is an object of the present invention to provide a new and improved method and system to create and use an algae based food supplement for but not limited to beef cattle.

Still another object of the present invention is to provide a new and improved algae food supplement which provides all of the advantages of the prior art, while simultaneously overcoming some of the disadvantages normally associated therewith.

Yet another object of the present invention is to provide a new and improved method and system for new and improved algae and algae food supplement that is commercially available such that public awareness is garnered and environmental improvement is created in regards to $CO_2$ reduction.

An even further object of the present invention is to provide a new and improved food supplement that provides the benefit of Omega-3 to the consumer with the ability to eat red meat which is far healthier than conventional red meat having a moderate or high degree of marbling, because heart healthy omega 3's counteract the negative health consequences of saturated fats present in the meat.

Still an even further object of the present invention is to provide an optimal yield rate of algae growth, approximately 25% or more of Omega-3 DHA and or EPA composition in harvested algae, approximately 50% of total fats in the algae, a consistent feedlot weight gain of 3 lbs/day per animal meeting industry standards, an increase of 10 to 20 times the healthy Omega-3 DHA and EPA in beef ready for market, and a possibly decrease of saturated fats in beef ready for market.

It is still further an object of the present invention to provide a new and improved method and system to create and use an algae based food supplement for cattle and buffalo for producing a better heart healthy food product from the cattle and buffalo or to generally feed and nourish cattle and buffalo.

It is further contemplated the invention may be utilized for the general feeding of other animals, such as but not limited to buffalo. It is contemplated that buffalo may be used a livestock for meat.

It is a further invention of this produce to modify the traditional modern feedlot composition substantially by reducing rolled corn and substituting wheat or barley with much lower fat content to then allow much higher amounts of algae to be fed the cattle without suppressing the total feed intake of the cattle due to too much fat. In addition, reducing corn lowers Omega 6, which is believed to be too high in the red meat diet resulting in arterial inflammation and illness.

These, together with other objects of the invention, along with the various features of novelty, which characterize the invention, are pointed out with particularity in the claims annexed to and forming a part of this disclosure. For a better understanding of the invention, its operating advantages, and the specific objects attained by its uses, reference should be had to the accompanying descriptive matter in which there are illustrated preferred embodiments of the invention.

BRIEF DESCRIPTION OF THE PICTORIAL ILLUSTRATIONS, GRAPHS, DRAWINGS, AND APPENDICES

The invention will be better understood and objects other than those set forth above will become apparent when consideration is given to the following detailed description thereof. Such description makes reference to the annexed pictorial illustrations, graphs, drawings, and appendices.

FIG. 1 is generally a graphical representation of concentration of fatty acids per gram tissue.

DETAILED DESCRIPTION

In a preferred embodiment, the composition generally comprises algae as a food supplement for animals such as but not limited to beef cattle. It is a further object of the present invention to provide a new and improved method and system to create and use an algae based food supplement for animals such as but not limited to buffalo, cattle, and other meat sources for human consumption that is more heart healthy as further described below.

It is understood that the following description of said components is not limited to exact percentages, quantities, or ingredients and that it is understood equivalent ingredients known in the art may be substituted or added. The current invention contemplates a unique algae-based cattle feed production system that will result in the commercial production of cattle feed with healthier fat content that may also include the capture and disposable of $CO_2$ from power generation.

There are more than 30,000 cultivars identified and catalogued to date. The current invention may utilize some specific cultivars of algae that readily produce high levels of DHA lipids, Docosahexaeonic Acid (DHA) a n-3 Polyunsaturated Fatty Acid (PUFA) has been associated with decreasing levels of cardiovascular disease, atherosclerosis, inflammation, arrhythmia, and circulating triglyceride levels while increasing neural development and visual acuity (National Academy of Sciences, 2002; Knapp et al., 2003). These lipids can be either extracted from the harvested algae, or the harvested algae can be condensed into a slurry, or can be dried and can be fed whole, directly to cattle. The specific algae cultivar chosen becomes an ingredient in the total feeding process for the cattle and it will result in the development of increased DHA and eicosapentaenoic acid, EPA, polyunsaturated fats in the finished beef.

The current invention may utilize (1) a cultivar that produces high levels of DHA and or EPA; and (2) a growing environment (algae farm/bioreactor) that includes feeding the algae with a carbon source as carbohydrate (such as sugar) This algae growth system maximizes algae growth and the production of the omega 3's in the maximum amounts, and grows it at relatively low cost.

This invention does not include the technology for growing the algae itself. That technology is developed and patented by others. This invention choses the algae to be grown in the algae growing system, especially for its ability both to produce high omega 3's and also to have a tough cell wall which will allow the algae to protect the omega 3's as the algae transits the rumen into the small intestine. Also this invention employs the whole algae in a feeding protocol which maximizes the intake of omega 3's, while it does not suppress the total feed intake, and does not reduce the commercially ideal average daily gain of the cattle in the feed yard.

It is contemplated that it is desirable to achieve not only sufficient growth rates and high levels of recoverable fat content in the algae "crop.", but relatively high percentages of polyunsaturated fats in relation to total fats. The saturated fats are not useful in producing Omega-3's in cattle, but reduce the total feed intake if total fats reach approximately 8% of the total feed intake. A goal is to feed large amounts of algae containing large amounts of DHA and or EPA without reducing food intake to maintain industry standards of daily weight gain in the cattle of about 3.5 lbs/day These success factors depend in turn upon the selection of the best algae of which there are thousands of existing candidates and more being genetically engineered and the performance of the algal growth with a bioreactor environment.

It is contemplated that the current invention may utilize algae strains found in the current art. It is also contemplated that the current invention may utilize new and non-prior art algae strains with the desired characteristics. It is still further contemplated the current invention may use whole, not processed, algae as a feed for cattle and bison, as feeding Omega-3's directly, that is without the protection of the Omega-3's by the cell wall while in the rumen, is not suitable for the digestive system of cattle which otherwise destroys the polyunsaturated fats, rendering them un-useful for absorption in the small intestine and depositing Omega 3's in the marbling of the meat.

One embodiment may dewater the algae to about 18% and deliver the whole unprocessed algae immediately to a nearby feed yard for mixing with the modified traditional feed ration. Whole algae may also be dried and fed directly to cattle for a source of protein, carbohydrate, and lipids.

It is also contemplated growing a very particular kind of algae with appropriate environmental growing conditions including nutrition and stress protocols that enhance the existing but underutilized genetic proclivity of the algae strain to maximize high value PUFA's (polyunsaturated fatty acids) containing the Omega-3 fatty acids DHA and EPA. These PUFA algae can be used whole/dried and or wet and mixed directly with the cattle feed. Feed with such shows the ability of cattle to ingest and incorporate the DHA and EPA into the marbling fat of the meat, or into the muscle cell walls, or into the interior of the muscle cells, transforming the beef into a new form of "healthy beef", which may improve the heart health and central nervous system of the consumer. It is contemplated the current invention may utilize different dosages, timing of feed, duration, deposition rates and deposition position.

It is contemplated to utilize an algae having a cultivar with high Omega-3's and appropriate cell wall. The cell walls of micro algae can naturally be composed of very different materials and having very different degrees of digestibility in the normal rumen of cattle, which is highly acidic, and the small intestine, which is highly basic. It is contemplated to utilize an algae which produces a cell wall that is not digestible in the rumen, where the Omega-3's inside are protected from hydrogenation during digestion, but the cell wall does break in the small intestine, releasing the Omega-3's. In effect, the appropriate cell wall behaves like a time release capsule.

Now referring generally to the figures and more in particular to FIG. 1, the graph generally shows the increase of EPA and DHA with three alternate feed rations of no algae, modest algae, and rich algae. The data was obtained with feed demonstrations at Oklahoma State University. The demonstration used a commercially available product, Martek GOLD, which is particularly high in DHA and not high in EPA. The demonstrations generally utilized a mix of dry algae to modified mixtures of typical cattle feed rations and provided a successful conclusion of the high depositions of EPA and DHA into the muscle and fat within the muscle of beef cattle.

It is also contemplated that the current invention may provide algae feed rations without compromising the average daily weight gain of the cattle, as the daily gain of cattle must be as good as with non-algae rations, to produce the desired outcome of not significantly increasing the total cost of the fully fed steer.

It is known in the industry to provide algae for some other end products. High value algae particularly containing high amounts of DHA algae have been commercialized by Martek Biosciences based in Baltimore, Md. The Martek algae contain the right cell wall and the right amounts of DHA but are heterotrophic, meaning they are fed sugar, and the growing and containment system is expensive, making the product very expensive. Their products are marketed to egg production and infant baby formulas and many other products. It is contemplate the current invention may be utilized with heterotrophic production systems which are much lower in cost than Martek's system While the current price of heterotrophic Martek algae is $19,000 per ton, it is expected that other systems may produce the requisite algae for $3,000 to $4000 per ton. The value of algae for beef is much greater than for biodiesel, rendering this use of algae more economical in the near term.

Docosahexaeonic Acid (DHA), an n-3 Polyunsaturated Fatty Acid (PUFA) has been associated with decreasing levels of cardiovascular disease, atherosclerosis, inflammation, arrhythmia, and circulating triglyceride levels while increasing neural development and visual acuity (National Academy of Sciences, 2002; Knapp et al., 2003). Until now, DHA has been sourced from fish oil, fishmeal, fresh fish and algae. It is contemplated that the current invention may use various feeds for cattle to increase the proportion of healthy to unhealthy fat in their "marbling." Increased levels of DHA in cattle feeds has been shown to additionally increase the levels of conjugated linoleic and vaccenic acids in ruminant fat; unsaturated fatty acids are also implicated in enhanced human health benefits The market for algae as cattle feed is also potentially huge. It would take the daily production of 200,000 pounds to supply the feedlot cattle for the "natural Beef" market (without hormonal or antibiotic chemicals), Another 400,000 pounds per day would supply algae to cattle destined for the white tablecloth market. And 20,000,000 pounds per day would be needed to supply the more than 10,000,000 cattle in U.S. feed yards in the Corn Belt from the Texas Panhandle to South Dakota.

The current invention contemplates the utilization of a system wherein the location of algae growth facility, and or cattle are optimized with a preferred embodiment locating the algae growth facility, and feedlot for the cattle in such a manner that no processing or drying is needed, and no or little transportation is needed between same.

It is contemplated to produce Omega-3 rich algae feed for beef cattle which in turn results in a potentially healthier meat product containing higher levels of protective fats and lower levels of unhealthy saturated fats than the market standard.

In a preferred embodiment, an array of algae growing facilities will be located close to the feedlots. The close location will both minimize transportation expenses and allow for the algal slurry, containing a 20:80 algae-water mixture, to be delivered directly to feed cattle without drying it first. This arrangement may serve as an efficient design model for the commercial algae-fed cattle industry. It is also contemplated the algae will be dewatered to a ratio of 18% algae by weight for easy pumping and cost-effective trucking to a feed yard for the cattle. It is contemplated that avoiding the cost of drying the algae will reduce costs and processing time. The algae/water mixture may be sprayed on the primary cattle feed in the "bunk" as a top dressing, or it may be mixed, as is customary, in the feed truck itself to provide a uniform algae/feed mixture.

In a preferred embodiment of the invention, whole algae may be added immediately to typical but adjusted cattle feed rations to optimize the average daily gain of the cattle at about 3 pounds per day. The concept of feeding algae to cattle only for its caloric food value to the cattle itself or to improve the health of the cattle itself is not unique. However, the concept of feeding algae to cattle to shift the marbling fat from saturated fat to polyunsaturated fats or to produce more polyunsaturated fats in the muscle tissue is unique.

Presently food-grade algae, high in Omega-3 DHA, is expensive ($19,000 per ton) and thus not practical to feed animals in large quantities. The current invention contemplates producing algae containing DHA and EPA Omega-3's at $3,000 per ton. This will allow a unique cattle feeding program resulting in substantially reduced saturated fats and an increase in healthy polyunsaturated fats.

With algae fed beef, the current invention contemplates ten times or more of Omega-3's and a substantial reduction of saturated fats. It is further contemplated the health benefits of reducing saturated fats and increasing unsaturated fats with Omega-3's, will attract consumers to the product who will pay a premium, which is not expected to be more than 10 percent above standard beef and is less expensive than beef with no antibiotics and no hormonal implants, or than organic beef. The price of existing niche beef, which is sold as "healthy beef", is as much as twice the price of regular commercial beef. This very high price is likely due to the very low sales volumes and inefficiencies of the producers. At this time, the price of beef free of chemical residuals from antibiotics or hormonal implants is $5.00 higher than comparable beef. The cost of algae supplement is predicted to add about $0.40 to the wholesale cost of beef.

A cattle feeding demonstration has proven the concept that algae can be fed to cattle and the meat can contain high amounts of Omega-3 DHA and EPA, such as are available otherwise in salt-water white fish. Algae was utilized from the Martek Corporation that had high Omega-3. The Omega-3 of Martek is about 56% lipids (fat) of which about half or 24% of the algae weight is DHA, and 2% is EPA.

It is noteworthy that Omega-3's cannot be fed to cattle directly, such as from fish oil in high quantities, but can be fed the Omega-3's in algae. In previous feeding trials by others it was determined that feeding cattle fish oil containing Omega-3's depressed rumen function. Microorganisms in the cattle's rumen hydrogenate the Omega-3's polyunsaturated fatty acids into saturated fats so that the fish oil could not supply unsaturated fats in the small intestine where they could be absorbed. In contrast, the current invention utilizes algae that have a cell wall that has a natural advantage. The cell wall is not as readily and as rapidly broken down in the rumen. More of the algae cell is transmitted to the duodenum intact where the pH change and digestive enzymes break down the algae releasing the Omega-3's to be absorbed in the small intestine. The valuable Omega-3's need to be microencapsulated in order to be absorbed intact. The algal cultivars of the current embodiment will feed to cattle have the Omega-3's microencapsulated naturally. Hence, the algae provide a natural food supplement to improve the healthiness of beef.

It is also contemplated to utilize different types of cultivar selection programs to develop more efficient and effective "seeds" for use in feeding cattle. A variety of species from multiple algal divisions, classes, order, families, genera and species may be utilized. Optimal culture patterns may use a variety of potential cultivars picked for their growth rates, nutrition profiles, or production of unique secondary metabolites. Initial lab efforts by a DOE funded project in Arizona resulted in the down-selection of a few potential cultivars that were subsequently grown in large outdoor cultivators. A summary of those strains investigated and potential for use are illustrated in below.

|  | Algae Species | | |
| --- | --- | --- | --- |
|  | *Nannochloropsis* 0603 | *Selenastrum* 1227 | *Scenedesmus* 0108 |
| Culturing Period (d) | 206 | 40 | 210 |
| Growth Rate(g/m2/d) Average | 11 | 17 | 22 |
| Growth Rate(g/m2/d) Maximal | 18 | 26 | 29 |
| Total Volume Harvested Over Period (L) | 122,500 | 18,700 | 133,900 |
| Culture Temp (c.) | 10-25 | 20-30 | 10-40 |

It is contemplated to utilize algal cultivar based on selection criteria that extend beyond biological parameters and may include its ability to be harvested, transported, and processed. Although these characteristics may be secondary to utilizing a cultivar that grows rapidly, producing algae that can be filtered easily or settle naturally may greatly reduce harvesting operational expenses, which can have a significant effect on the cultivar selection process.

Potential cultivar candidates characteristics may include high production rates, accumulates significant amounts of oil under the correct conditions and can partially settle without any energy or chemical input and are not genetically modified or enhanced. In a preferred embodiment species may consist of 2-8% lipids with the understanding other culturing conditions in the large-scale culturing systems may accumulate up to at least 40% of the biomass as extractable lipid. A preferred embodiment may grow nannochloropsis with 39% lipids of which 9% was EPA. Other preferred embodiment may be *Koliella antartica* a euryhaline (0-3 5 ppt) and eurythermal (0-60° F.) alga, which thrive in low-light conditions. Additionally *Chlorella saccharophila* represents another potential winter species. Although a global genus, many *Chlorella* are found in waters of 40° F. (night) to 65° F. (day). Some *Chlorella* varieties have a high Omega-3 fatty acids and astuxanthin (pigment) content.

The current invention contemplates utilizing an algae such as a particular *schizochytrium* with similar constituents to DHA GOLD™ from MARTEK also known as MARTEK GOLD. Generally, the total fat may be 56% and the percentage of fat that is DHA and EPA may generally be 44%. It is understood that DHA GOLD™ is a fermentation product, and due to the characteristics of the producing organism, some variability in the nutritional values will be observed from lot to lot. The basic components (g/100) may be but is not limited to moisture 2.03, protein 6.66, crude fiber 4.5, ash 8.81, crude fat 55.57, and carbohydrates (by subb'n) 12.43. The minerals in the algae (g/100) may be but is not limited to calcium 0.03, sodium 2.21, potassium 0.51, magnesium 0.11, and phosphorus 0.13.

| The fatty acid profile (% FFA) may be but is not limited to: | | |
|---|---|---|
| 12:0 | Lauric | 0.3 |
| 14:0 | Myristic | 8.5 |
| 15:0 | Pentadecanole | 0.3 |
| 16:0 | Palmitic | 23.2 |
| 18:0 | Stearic | 0.8 |
| 24:0 | Linoceric | 0.9 |
| 18.3n6 | Lignolenic | 0.4 |
| 18:4n3 | Octadecatetranoaic | 0.4 |
| 20:3n6 | Homogammallnoieic | 1.56 |
| 20:4n7 | Elcosatetranoic | 0.9 |
| 20:3n3 | EPA | 1.9 |
| 22:5n6 | OPA | 17.7 |
| 22:6n3 | DHA | 42.3 |

| The amino acid profile (g/100 g) may be but is not limited to: | |
|---|---|
| Tryptophan | 0.16 |
| Aspartic Acid | 1.25 |
| Threonine | 0.46 |
| Serine | 0.49 |
| Glutamic Acid | 3.86 |
| Proline | 0.50 |
| Glycine | 0.60 |
| Alanine | 0.70 |
| Cystine | 0.15 |
| Valine | 0.74 |
| Methionine | 0.27 |
| Isoleucine | 0.37 |
| Leucine | 0.66 |
| Tyrosine | 0.29 |
| Phenylalanine | 0.42 |

| The amino acid profile (g/100 g) may be but is not limited to: | |
|---|---|
| Histidine | 0.22 |
| Lysine (total) | 0.42 |
| Arginine | 1.48 |

| The vitamin content may be but is not limited to: | | |
|---|---|---|
| Biotin | 0.38 | mg/100 g |
| Cholline | 2.20 | mg/100 g |
| Folic Acid | 1.28 | mg/100 g |
| Niacin | 5.756 | mg/100 g |
| Vitamin A true retinol | <440 | IU/100 g |
| Beta carotene | 6,440 | IU/100 g |
| Vitamin B1 thiamine HCl | 2.81 | mg/100 g |
| Vitamin B2 riboflavin | 3.15 | mg/100 g |
| Vitamin B6 pyridoxine | 1.90 | mg/100 g |
| Vitamin C ascorbic acid | 14.1 | mg/100 g |
| Vitamin E alpha tocopherol | <0.7 | IU/100 g |
| Vitamin B12 cyanocobalamin | 93.6 | ug/100g |
| Pantothenic acid | 5.33 | mg/100 g |

It is understood that feedlots for such animals as cattle attempt to maximize the meat on an animal while balancing the time spent on the feedlot with food intake and costs associated thereof. It is typical that cattle would need approximately about 5.5 to 6.5 pounds of diet for an animal to gain 1 pound assuming normal finishing diet. Also, it is understood that the animals do not enter the feedlot until they already weigh 600 to 900 pounds. During that time, they consume mostly forage prior to entering the feedlot. Most producers use forage because it is cheaper and a good use of fiber that would otherwise not be harvested.

Cattle are normally kept on the feedlot until for between 150 and 240 days. During this time period, they may gain 500 to 600 pounds. It is not unusual for animals to arrive at 7 to 9 months of age and receive 100% grass feed to help maintain rumen health for the first four days. Different feedlots use different types of food whereas some rations may be comprised of seven ingredients, including corn, soy, alfalfa, straw, and wet grain distillers that are by-products of the ethanol industry. These feeds range from 0% corn to 75% corn.

The typical steer arrives at the feedlot weighing approximately 800 pounds and on average, leaves 6 months later, having eaten 5,000 pounds of feed to gain 600 pounds in weight. Cattle are normally fed 25 pounds of grain and small amounts of other constituents. For commercial viability in the feed yard, the average cow must consume enough feed for a weight gain of approximately 3.5 pounds a day.

The current invention contemplates providing a maximum amount of algae, which a cow could consume without suppressing the remainder of the feed intake and without reducing the daily gain as measured by pounds of body weight per day. In a preferred embodiment, a daily intake of algae may contain approximately 24% Omega-3's, DHA and EPA in order to maximize the deposition of Omega-3's in the marbling. It is also contemplated that an optimum diet may eliminate one of the normal constituents of pig fat and or reduced corn and increase of algae, such as but not limited to MARTEK GOLD, to obtain the correct choleric value of the total feed. It is contemplated that feeding too much algae may suppress the diet of the animal. By example, 2 pounds of Martek algae combined with the other ingredient and ingested as above with a high amount of oil in the corn resulted in the cow eating half its total feed for the day and, resulted in the cow not gaining sufficient weight per day.

A preferred embodiment provides 0.8 to 1.0 pounds of Martek algae per day. It is contemplated the suppression of daily intake may be caused by an excess amount of fat in the diet. Beef cattle reduce food intake by themselves when the fat composition of the feed exceeds 8%. Corn, the main ingredient in a fed lot ration, is 5.6% fat from corn oil and therefore left a small window of approximately 2% fat, which could be added by the algae without suppressing the diet. One pound of algae, which contained 50% fat, half saturated fat and half polyunsaturated fat, would contain approximately 2% fit by weight in the feedlot ration. The 2% fat in the algae plus the nearly 6% fat in the corn totaled approximately 8% which is the daily limit for beef cattle.

It is contemplated to utilize a new feedlot ration substituting wheat and/or barley for corn. Wheat or barley contain approximate 2% fat and can substitute for corn for the high calorie carbohydrate in the ration. This leaves approximately 6% fat that could be added by the algae. This would allow an additional 1.5 pounds of fat, which would be present in 3 pounds of algae from Martek, or 6 pounds of other possible algae. It is contemplated to substitute wheat or barley for corn and provides 4 pounds of algae rather than 1 pound. Therefore, another preferred embodiment may include utilizing barley instead of and or with corn. It is contemplated to utilize 2 to 3 pounds of algae, such as but not limited to MARTEK GOLD and reducing the barley or wheat ration slightly to maintain total caloric intake.

A preferred embodiment may include the use of algae without whole corn. It is contemplated to utilize wheat and corn gluten wherein the total fat content is under 8% and around 6%, and wherein the algae content is higher than with whole corn, which has more fat from corn oil. A preferred embodiment may contain wheat 56.5%, corn gluten feed 20.0%, alfalfa hay fair 4.75%, prairie hay 5.0%, algae 7.5%, wheat midds 1.0%, urea 0.32%, potassium chloride 0.3%, limestone at 38% 1.65%, salt 0.25%, manganous oxide 0.002%, zinc sulfate 0.015%, magnesium oxide 0.10%, vitamin a-30,000 0.004%, vitamin e-50% 0.0022%, corn dent No. 2 2.5767%, rumensin 90 0.0188%, and tylan 40 0.0113%. It is understood that the amount may be approximate and the invention may or may not include all the same elements.

It is therefore contemplated to provide a method for increasing the omega-3 highly unsaturated fatty acid content of meat for human consumption comprising feeding algae to cattle and or buffalo without suppressing the remainder of the feed intake of said cattle and without reducing the daily gain as measured by pounds of body weight per day of said cattle and or buffalo wherein said algae comprises an omega-3 unsaturated fatty acid content of about 25% percent of total weight in at effective amount to increase the content of omega-3 high unsaturated fatty acids in said beef.

Furthermore, it is contemplated the method may utilize an omega-3 unsaturated fatty acid content of about 24 percent DHA, and or about 2 percent EPA, or with higher ratios of EPA to DHA. The effective amount is about 0.8 to 1.0 pounds of said algae per day.

A number of implementations have been described herein. Nevertheless, it will be understood that various modifications may be made. Accordingly, other implementations are within the scope of the following claims. Changes may be made in the combinations, operations, and arrangements of the various steps, elements, and amounts described herein without departing from the spirit and scope of the invention.

The invention claimed is:

1. A method for increasing omega-3 highly unsaturated fatty acid content in beef for human consumption, wherein said method consists essentially of feeding to cattle, without suppressing the remainder of feed intake of said cattle and without reducing daily gain of said cattle measured by pounds of body weight per day, an effective amount of:
   a *Schizochytrium* and
   corn, and
wherein the effective amount of the *Schizochytrium* is between about 0.8 and about 1.0 pounds per day and omega 3 highly unsaturated fatty acid content is increased in the beef of said cattle.

2. A method for increasing omega-3 highly unsaturated fatty acid content in beef for human consumption, wherein said method consists essentially of feeding to cattle, without suppressing the remainder of feed intake of said cattle and without reducing daily gain of said cattle measured by pounds of body weight per day, an effective amount of:
   a *Schizochytrium* and
   at least one grain selected from the group consisting of wheat and barley, and
wherein the effective amount of the *Schizochytrium* is between about 2 to about 3 pounds per day and omega 3 highly unsaturated fatty acid content is increased in the beef of said cattle.

3. A method for increasing omega-3 highly unsaturated fatty acid content in beef for human consumption, wherein said method consists essentially of feeding to cattle, without suppressing the remainder of feed intake of said cattle and without reducing daily gain of said cattle measured by pounds of body weight per day, an effective amount of:
   a *Schizochytrium;*
   corn; and
   at least one ingredient selected from the group consisting of soy, alfalfa, straw and wet grain distillers, and
wherein the effective amount of the *Schizochytrium* is between about 0.8 and about 1.0 pounds per day and omega 3 highly unsaturated fatty acid content is increased in the beef of said cattle.

4. A method for increasing omega-3 highly unsaturated fatty acid content in beef for human consumption, wherein said method consists essentially of feeding to cattle, without suppressing the remainder of feed intake of said cattle and without reducing daily gain of said cattle measured by pounds of body weight per day, an effective amount of:
   a *Schizochytrium;*
   corn; and
   at least one ingredient selected from the group consisting of soy, alfalfa, straw and wet grain distillers, and
wherein the effective amount of the *Schizochytrium* is between about 2 to about 3 pounds per day and omega 3 highly unsaturated fatty acid content is increased in the beef of said cattle.

* * * * *